(12) United States Patent
Cantet et al.

(10) Patent No.: US 11,807,863 B2
(45) Date of Patent: Nov. 7, 2023

(54) **RESISTANCE TO CUCUMBER GREEN MOTTLE MOSAIC VIRUS IN *CUCUMIS SATIVUS***

(71) Applicant: Seminis Vegetable Seeds, Inc., St. Louis, MO (US)

(72) Inventors: Melissa C. Cantet, Rotterdam (NL); Belgin Cukadar, Rotterdam (NL); Maarten de Milliano, Bergschenhoek (NL); Antoon Stekelenburg, Houten (NL)

(73) Assignee: SEMINIS VEGETABLE SEEDS, INC., St. Louis, MO (US)

( * ) Notice: Subject to any disclaimer, the term of this patent is extended or adjusted under 35 U.S.C. 154(b) by 24 days.

(21) Appl. No.: 17/198,226

(22) Filed: Mar. 10, 2021

(65) Prior Publication Data
US 2021/0285008 A1    Sep. 16, 2021

Related U.S. Application Data

(60) Provisional application No. 62/989,347, filed on Mar. 13, 2020.

(51) Int. Cl.
*C12N 15/82* (2006.01)
*C12Q 1/6895* (2018.01)
*C07K 14/415* (2006.01)

(52) U.S. Cl.
CPC ........ *C12N 15/8283* (2013.01); *C07K 14/415* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | |
|---|---|---|
| 7,459,604 B2 | 12/2008 | Onstenk E. V. Fierens et al. |
| 8,766,041 B2 | 7/2014 | Mazereeuw et al. |
| 8,779,241 B2 | 7/2014 | Mazereeuw et al. |
| 10,226,018 B2 | 3/2019 | Harring et al. |

(Continued)

FOREIGN PATENT DOCUMENTS

| | | |
|---|---|---|
| WO | 2009129314 | 10/2009 |
| WO | 2019032427 | 2/2019 |

OTHER PUBLICATIONS

Majeed et al. "Role of SNPs in determining QTLs for major traits in cotton" 2019 J. Cotton Res. 2(5): https://doi.org/10.1186/s42397-019-0022-5 (13 total pages). (Year: 2019).*

(Continued)

*Primary Examiner* — Matthew R Keogh
*Assistant Examiner* — Rebecca Stephens
(74) *Attorney, Agent, or Firm* — DENTONS US LLP; Alissa Eagle

(57) ABSTRACT

Cucumber plants (*Cucumis sativus*) exhibiting increased resistance to Cumber Green Mottle Mosaic Virus (CGMMV) are provided, together with methods of producing, identifying, or selecting plants or germplasm with a CGMMV resistance phenotype. Such plants include cucumber plants comprising recombinant chromosomal segments conferring CGMMV resistance. Compositions, including novel polymorphic markers for detecting plants comprising introgressed virus resistance alleles, are further provided.

9 Claims, 2 Drawing Sheets

Specification includes a Sequence Listing.

(56) References Cited

U.S. PATENT DOCUMENTS

2017/0016022 A1    1/2017    Van Dun et al.
2018/0223307 A1    8/2018    de Joode et al.

OTHER PUBLICATIONS

Wei et al. "Rapid identification of fruit length loci in cucumber (*Cucumis sativus* L.) using next-generation sequencing (NGS)-based QTL analysis" 2016 Sci. Reports 6:27496 DOI:10.1038/srep27496 (11 total pages) (Year: 2016).*

Day-Rubenstein and Heisey "Chapter 3.1: Crop Genetic Resources" pp. 50-58 IN Agricultural Resources and Environmental Indicators, 2006 Edition, EIB-16 Economic Research Service USDA. (Year: 2006).*

Plant Inventory No. 168 of the United States Department of Agriculture, 1967 at p. 198; available at https://naldc.nal.usda.gov/download/39248/PDF (last visited Sep. 13, 2022). 2 page excerpt. (Year: 1967).*

Leibman et al. "Differential expression of cucumber RNA-dependent RNA polymerase 1 genes during antiviral defence and resistance" 2018 Mol. Plant Pathology 19(2): 300-312. (Year: 2018).*

International Search Report and Written Opinion regarding International App. No. PCT/US21/21689, dated Jul. 9, 2021.

Li et al., Syntenic relationships between cucumber (*Cucumis sativus* L.) and melon (*C. melo* L.) chromosomes as revealed by comparative genetic mapping, BMC Genomics 12(396):1-14, 2011.

Crespo et al., "Resistance to Cucumber green mottle mosaic virus in Cucumis sativus" Euphytica, 2018, 214:201-211.

Leibman et al., "Differential expression of cucumber RNA-dependent RNA polymerase 1 genes during antiviral defence and resistance" Mol. Plant Pathol. 2018, 19(2):300-312. Epub Feb. 8, 2017.

Liu et al., "Quantitative proteomics identifies 38 proteins that are differentially expressed in cucumber in response to cucumber green mottle mosaic virus infection" Virology Journal, 2015, 12:216.

Liu et al., "High-Throughput Sequencing Identifies Novel and Conserved Cucumber (*Cucumis sativus* L.) microRNAs in Response to Cucumber Green Mottle Mosaic Virus Infection" PLOS ONE, Jun. 15, 2015;10(6):e0129002.

Wolf et al., "The Plant Breeders' Dream Come True: Editing Non-Transgenic Cucumber for Broad Virus Resistance Using CRISPR/Cas9 Technology" Proceedings of Cucurbitaceae 2016, the XIth EUCARPIA Meeting on Genetics and Breeding of Cucurbitaceae. Jul. 24-28, 2016, Warsaw, Poland.

Todd C. Wehner, Cucurbit Genetics Cooperative Report 13:1-3 (article 1) 1990.

* cited by examiner

SEQUENCE LISTING

```
<160> NUMBER OF SEQ ID NOS: 48

<210> SEQ ID NO 1
<211> LENGTH: 121
<212> TYPE: DNA
<213> ORGANISM: Artificial Sequence
<220> FEATURE:
<223> OTHER INFORMATION: Nucleotide sequence of Marker CGMMV_1
<220> FEATURE:
<221> NAME/KEY: variation
<222> LOCATION: (61)..(61)
<223> OTHER INFORMATION: Variant at position 61: G

<400> SEQUENCE: 1
ctcgctatct tgaagtttgt cagtctgcat attgtttata ttttcatat taatgcaaaa      60 tgttacttga aacatgaggg gcatgttgag atgttgagaa tcccacatcg aaaagaccat    120
g                                                                    121

<210> SEQ ID NO 2
<211> LENGTH: 28
<212> TYPE: DNA
<213> ORGANISM: Artificial Sequence
<220> FEATURE:
<223> OTHER INFORMATION: Forward primer for Marker CGMMV_1

<400> SEQUENCE: 2
cttgaagttt gtcagtctgc atattgtt                                        28

<210> SEQ ID NO 3
<211> LENGTH: 25
<212> TYPE: DNA
<213> ORGANISM: Artificial Sequence
<220> FEATURE:
<223> OTHER INFORMATION: Reverse primer for Marker CGMMV_1
```

<400> SEQUENCE: 3
ggtcttttcg atgtgggatt ctcaa    25

<210> SEQ ID NO 4
<211> LENGTH: 21
<212> TYPE: DNA
<213> ORGANISM: Artificial Sequence
<220> FEATURE:
<223> OTHER INFORMATION: Probe 1 for marker CGMMV_M1

<400> SEQUENCE: 4
tgtttcaagt aacattttgc a    21

<210> SEQ ID NO 5
<211> LENGTH: 21
<212> TYPE: DNA
<213> ORGANISM: Artificial Sequence
<220> FEATURE:
<223> OTHER INFORMATION: Probe 2 for marker CGMMV_M1

<400> SEQUENCE: 5
tgtttcaagt aacctttgc a    21

<210> SEQ ID NO 6
<211> LENGTH: 269
<212> TYPE: DNA
<213> ORGANISM: Artificial Sequence
<220> FEATURE:
<223> OTHER INFORMATION: Nucleotide sequence of Marker CGMMV_2
<220> FEATURE:
<221> NAME/KEY: misc_feature
<222> LOCATION: (26)..(136)
<223> OTHER INFORMATION: n is a, g, c or t
<220> FEATURE:
<221> NAME/KEY: misc_feature
<222> LOCATION: (36)..(36)
<223> OTHER INFORMATION: n is a, g, c or t
<220> FEATURE:
<221> NAME/KEY: misc_feature
<222> LOCATION: (76)..(76)
<223> OTHER INFORMATION: n is a, g, c or t
<220> FEATURE:
<221> NAME/KEY: misc_feature
<222> LOCATION: (128)..(128)
<223> OTHER INFORMATION: n is a, g, c or t
<220> FEATURE:
<221> NAME/KEY: variation
<222> LOCATION: (136)..(136)
<223> OTHER INFORMATION: Variant at position 136: T
<220> FEATURE:
<221> NAME/KEY: misc_feature
<222> LOCATION: (254)..(254)
<223> OTHER INFORMATION: n is a, g, c or t

<400> SEQUENCE: 6
tgtatgcata tttaagtgag aatttntta cctttnaggt ttggctaacc catatttag    60 gggaggtgct gccganttt tgtagaatt ttatattact tgttctatta taagtttaag    120
ttgaatantg cttggattca aaaagcgttc ttataacacg atctaggtta ggagggaaa    180 tctagaatga ggtgtgacat gtattcttta ggactcaatc atttctccca ttcaagcaac    240
cataagagta gtangatata cacacacat    269

<210> SEQ ID NO 7
<211> LENGTH: 26
<212> TYPE: DNA
<213> ORGANISM: Artificial Sequence
<220> FEATURE:
<223> OTHER INFORMATION: Forward primer for Marker CGMMV_2

```
<400> SEQUENCE: 7
aggtttggct aacccatatt ttaggg                                              26

<210> SEQ ID NO 8
<211> LENGTH: 23
<212> TYPE: DNA
<213> ORGANISM: Artificial Sequence
<220> FEATURE:
<223> OTHER INFORMATION: Reverse primer for Marker CGMMV_2

<400> SEQUENCE: 8
cccctcctaa cctagatcgt gtt                                                 23

<210> SEQ ID NO 9
<211> LENGTH: 16
<212> TYPE: DNA
<213> ORGANISM: Artificial Sequence
<220> FEATURE:
<223> OTHER INFORMATION: Probe 1 for Marker CGMMV_2

<400> SEQUENCE: 9
cttggattca aaaagc                                                         16

<210> SEQ ID NO 10
<211> LENGTH: 15
<212> TYPE: DNA
<213> ORGANISM: Artificial Sequence
<220> FEATURE:
<223> OTHER INFORMATION: Probe 2 for Marker CGMMV_2

<400> SEQUENCE: 10
ttggtttcaa aaagc                                                          15

<210> SEQ ID NO 11
<211> LENGTH: 601
<212> TYPE: DNA
<213> ORGANISM: Artificial Sequence
<220> FEATURE:
<223> OTHER INFORMATION: Nucleotide sequence of Marker CGMMV_3
<220> FEATURE:
<221> NAME/KEY: variation
<222> LOCATION: (301)..(301)
<223> OTHER INFORMATION: Variant at position 301: T
<220> FEATURE:
<221> NAME/KEY: misc_feature
<222> LOCATION: (403)..(403)
<223> OTHER INFORMATION: n is g, a, c or t
<220> FEATURE:
<221> NAME/KEY: misc_feature
<222> LOCATION: (404)..(404)
<223> OTHER INFORMATION: n is g, a, c or t
<220> FEATURE:
<221> NAME/KEY: misc_feature
<222> LOCATION: (405)..(405)
<223> OTHER INFORMATION: n is g, a, c or t
<220> FEATURE:
<221> NAME/KEY: misc_feature
<222> LOCATION: (406)..(406)
<223> OTHER INFORMATION: n is g, a, c or t
<220> FEATURE:
<221> NAME/KEY: misc_feature
<222> LOCATION: (407)..(407)
<223> OTHER INFORMATION: n is g, a, c or t
<220> FEATURE:
<221> NAME/KEY: misc_feature
<222> LOCATION: (408)..(408)
<223> OTHER INFORMATION: n is g, a, c or t
<220> FEATURE:
<221> NAME/KEY: misc_feature
<222> LOCATION: (409)..(409)
```

-continued

```
<223> OTHER INFORMATION: n is g, a, c or t
<220> FEATURE:
<221> NAME/KEY: misc_feature
<222> LOCATION: (410)..(410)
<223> OTHER INFORMATION: n is g, a, c or t
<220> FEATURE:
<221> NAME/KEY: misc_feature
<222> LOCATION: (411)..(411)
<223> OTHER INFORMATION: n is g, a, c or t
<220> FEATURE:
<221> NAME/KEY: misc_feature
<222> LOCATION: (412)..(412)
<223> OTHER INFORMATION: n is g, a, c or t
<220> FEATURE:
<221> NAME/KEY: misc_feature
<222> LOCATION: (413)..(413)
<223> OTHER INFORMATION: n is g, a, c or t
<220> FEATURE:
<221> NAME/KEY: misc_feature
<222> LOCATION: (414)..(414)
<223> OTHER INFORMATION: n is g, a, c or t
<220> FEATURE:
<221> NAME/KEY: misc_feature
<222> LOCATION: (415)..(415)
<223> OTHER INFORMATION: n is g, a, c or t
<220> FEATURE:
<221> NAME/KEY: misc_feature
<222> LOCATION: (416)..(416)
<223> OTHER INFORMATION: n is g, a, c or t
<220> FEATURE:
<221> NAME/KEY: misc_feature
<222> LOCATION: (417)..(417)
<223> OTHER INFORMATION: n is g, a, c or t
<220> FEATURE:
<221> NAME/KEY: misc_feature
<222> LOCATION: (418)..(418)
<223> OTHER INFORMATION: n is g, a, c or t
<220> FEATURE:
<221> NAME/KEY: misc_feature
<222> LOCATION: (419)..(419)
<223> OTHER INFORMATION: n is g, a, c or t
<220> FEATURE:
<221> NAME/KEY: misc_feature
<222> LOCATION: (420)..(420)
<223> OTHER INFORMATION: n is g, a, c or t
<220> FEATURE:
<221> NAME/KEY: misc_feature
<222> LOCATION: (421)..(421)
<223> OTHER INFORMATION: n is g, a, c or t
<220> FEATURE:
<221> NAME/KEY: misc_feature
<222> LOCATION: (422)..(422)
<223> OTHER INFORMATION: n is g, a, c or t
<220> FEATURE:
<221> NAME/KEY: misc_feature
<222> LOCATION: (423)..(423)
<223> OTHER INFORMATION: n is g, a, c or t
<220> FEATURE:
<221> NAME/KEY: misc_feature
<222> LOCATION: (424)..(424)
<223> OTHER INFORMATION: n is g, a, c or t
<220> FEATURE:
<221> NAME/KEY: misc_feature
<222> LOCATION: (425)..(425)
<223> OTHER INFORMATION: n is g, a, c or t
<220> FEATURE:
<221> NAME/KEY: misc_feature
<222> LOCATION: (426)..(426)
<223> OTHER INFORMATION: n is g, a, c or t
<220> FEATURE:
<221> NAME/KEY: misc_feature
<222> LOCATION: (427)..(427)
<223> OTHER INFORMATION: n is g, a, c or t
<220> FEATURE:
<221> NAME/KEY: misc_feature
<222> LOCATION: (428)..(428)
<223> OTHER INFORMATION: n is g, a, c or t
<220> FEATURE:
<221> NAME/KEY: misc_feature
```

```
<222> LOCATION: (429)..(429)
<223> OTHER INFORMATION: n is g, a, c or t
<220> FEATURE:
<221> NAME/KEY: misc_feature
<222> LOCATION: (430)..(430)
<223> OTHER INFORMATION: n is g, a, c or t
<220> FEATURE:
<221> NAME/KEY: misc_feature
<222> LOCATION: (431)..(431)
<223> OTHER INFORMATION: n is g, a, c or t
<220> FEATURE:
<221> NAME/KEY: misc_feature
<222> LOCATION: (432)..(432)
<223> OTHER INFORMATION: n is g, a, c or t
<220> FEATURE:
<221> NAME/KEY: misc_feature
<222> LOCATION: (433)..(433)
<223> OTHER INFORMATION: n is g, a, c or t
<220> FEATURE:
<221> NAME/KEY: misc_feature
<222> LOCATION: (434)..(434)
<223> OTHER INFORMATION: n is g, a, c or t
<220> FEATURE:
<221> NAME/KEY: misc_feature
<222> LOCATION: (435)..(435)
<223> OTHER INFORMATION: n is g, a, c or t
<220> FEATURE:
<221> NAME/KEY: misc_feature
<222> LOCATION: (436)..(436)
<223> OTHER INFORMATION: n is g, a, c or t

<400> SEQUENCE: 11
tttatgtctt agtggataca tggtaactat tacctttctt taaatcaaac gttctatatt      60
catcattgtc aaaatggtta tagttcaatt ggtatatgta tgtgtcagtg acaaagaaat     120
atatagtttc aatcactcat ccctttatag tgaaggaaaa aaaatctcac tagcatttgt     180
taaaaaagat gtaagaccta tttcaattgt ctatttgttg gaatgccttg atttcatcat     240
gtggtgctac caataaccca attcaagagg tttagaaaag agcatatatt aactttctag     300
tctgggacgc ctaattatat ttcttctaac acactcttaa tgaacctagg tgttaatctt     360 tacattttc tattacttaa ttgttaattt cgtaacacta acnnnnnnnn nnnnnnnnn      420 nnnnnnnnnn nnnnnnccct gtcaataaaa attgcttaaa agaaattttg taacttagaa     480
agcttgtcta gatggtgaca aaaacacttc agttgttttt ctaaaatgac ttagttttaa     540
aataaatact caaaagttaa accaaacat gattgatttt actttattg ttaaaccaaa      600 c                                                                     601

<210> SEQ ID NO 12
<211> LENGTH: 28
<212> TYPE: DNA
<213> ORGANISM: Artificial Sequence
<220> FEATURE:
<223> OTHER INFORMATION: Forward primer for Marker CGMMV_3

<400> SEQUENCE: 12
ccaattcaag aggtttagaa aagagcat                                         28

<210> SEQ ID NO 13
<211> LENGTH: 29
<212> TYPE: DNA
<213> ORGANISM: Artificial Sequence
<220> FEATURE:
<223> OTHER INFORMATION: Reverse primer for Marker CGMMV_3

<400> SEQUENCE: 13
cacctaggtt cattaagagt gtgttagaa                                        29
```

<210> SEQ ID NO 14
<211> LENGTH: 16
<212> TYPE: DNA
<213> ORGANISM: Artificial Sequence
<220> FEATURE:
<223> OTHER INFORMATION: Probe 1 for Marker CGMMV_3

<400> SEQUENCE: 14
cgtcccaggc tagaaa                                                    16

<210> SEQ ID NO 15
<211> LENGTH: 16
<212> TYPE: DNA
<213> ORGANISM: Artificial Sequence
<220> FEATURE:
<223> OTHER INFORMATION: Probe 2 for Marker CGMMV_3

<400> SEQUENCE: 15
cgtcccagac tagaaa                                                    16

<210> SEQ ID NO 16
<211> LENGTH: 1029
<212> TYPE: DNA
<213> ORGANISM: Artificial Sequence
<220> FEATURE:
<223> OTHER INFORMATION: Nucleotide sequence of Marker CGMMV_4
<220> FEATURE:
<221> NAME/KEY: variation
<222> LOCATION: (855)..(855)
<223> OTHER INFORMATION: Variant at position 855: T

<400> SEQUENCE: 16
gaactgcttt ctcaaaacgt gttgaagaac cttttccagc tttcgaaatc tgactttgct      60
ttgcttggag aaagttgcag aggtatggta gatattactt catggagcca ttttttttc      120 attggactat ttaaggaggt tctagccacc ttgttttctt gtagaaaatt actcttttat     180
tttaaaggat tcactcgaga taaccacctt caagtttata gagaggtaat ttagtctaat    240
tgcatccatc atttctacgt tttaagaata agaattaagc atttggacat ttttcttcat    300
aatgtctata ctgttctgta tattgttttc tgcttgctat ttatctagaa aaatagatga    360
ggataaaatg tcatatttgt agataaatct cttattacat gcaatatgca taaaatatct    420
tgaacatata gaggatttct gggtgtaact aagcttgtac tttctcctat agaatgattc    480
ttaggccttc aactaaagtg ataaggaatc aaggattttg tctcttttca cacagtattt    540
tctttatgca taggaaagat caatctgatt gacatggatt ctctttccct tctttcaatc    600
gttcctgaaa aggaaattgt aatgtggaac ataaagatat acccgaccta gaaaagaaa     660 ggctcgtact tgttataaa tcttttggtt atttgttcat tcaggatcta actgaggaaa     720
atggtgaaga tctgctgcat tggagctggg tatgttggtg ggcctactat ggcagtgata    780
gcattaaaat gtcccacaat tgaagtagca gttgttgata tctctgtcgc gaagatctta    840
gcctggaata gtgatcaact ccccatatat gagcctggtc ttgatgaagt agtgaagcag    900
tgcagaggaa agaatctatt tttcagtaca gatgttgaaa ggcacgtctc agaggcagat    960
ataatctttg tttcagttaa cactccaaca aaaactcgag gccttggagc tggaaaagct   1020
gcactatag                                                           1029

<210> SEQ ID NO 17
<211> LENGTH: 25
<212> TYPE: DNA
<213> ORGANISM: Artificial Sequence

```
<220> FEATURE:
<223> OTHER INFORMATION: Forward primer for Marker CGMMV_4

<400> SEQUENCE: 17
gttgttgata tctctgtcgc gaaga                                          25

<210> SEQ ID NO 18
<211> LENGTH: 24
<212> TYPE: DNA
<213> ORGANISM: Artificial Sequence
<220> FEATURE:
<223> OTHER INFORMATION: Reverse primer for Marker CGMMV_4

<400> SEQUENCE: 18
ctacttcatc aagaccaggc tcat                                           24

<210> SEQ ID NO 19
<211> LENGTH: 19
<212> TYPE: DNA
<213> ORGANISM: Artificial Sequence
<220> FEATURE:
<223> OTHER INFORMATION: Probe 1 for Marker CGMMV_4

<400> SEQUENCE: 19
ctggaatagt gaccaactc                                                 19

<210> SEQ ID NO 20
<211> LENGTH: 19
<212> TYPE: DNA
<213> ORGANISM: Artificial Sequence
<220> FEATURE:
<223> OTHER INFORMATION: Probe 2 for Marker CGMMV_4

<400> SEQUENCE: 20
ctggaatagt gatcaactc                                                 19

<210> SEQ ID NO 21
<211> LENGTH: 493
<212> TYPE: DNA
<213> ORGANISM: Artificial Sequence
<220> FEATURE:
<223> OTHER INFORMATION: Nucleotide sequence of Marker CGMMV_5
<220> FEATURE:
<221> NAME/KEY: variation
<222> LOCATION: (344)..(344)
<223> OTHER INFORMATION: Variant at position 344: T

<400> SEQUENCE: 21
aaatatgctt ctttgcaaaa agataattct taatttgctt gctccgaaac ttgtatttgg    60
atagttcaat taggataacc atccattcaa acacgtattg acactagact cgttcacacc    120
agatttaccc ttaaattagt ttggggttat tatttctttt ttccgttctt acatgtgaat    180
ctgactaaaa taccagaata tggtgaattt tgaaagaag attaaagacg atctgactga     240
tttatttggt ttatggccac acgaactaag tttatttgtc ataaattctt gaatgtaatg    300
aattctaggg tgggatgcca gagattgtca aacctttcaa ggacgattca gctaagcaag    360
aaagatttga gcagttttta aaggaaaaat atcaaggagg cctgcgcact ggtgctcctg    420
ttggagctat taatatgtca gaagcagctc gtgcacgtga acgcttggac tttgaggctg    480
ctgcactata gtg                                                       493

<210> SEQ ID NO 22
<211> LENGTH: 25
<212> TYPE: DNA
```

```
<213> ORGANISM: Artificial Sequence
<220> FEATURE:
<223> OTHER INFORMATION: Forward primer for Marker CGMMV_5

<400> SEQUENCE: 22
ggatgccaga gattgtcaaa ccttt                                            25

<210> SEQ ID NO 23
<211> LENGTH: 29
<212> TYPE: DNA
<213> ORGANISM: Artificial Sequence
<220> FEATURE:
<223> OTHER INFORMATION: Reverse primer for Marker CGMMV_5

<400> SEQUENCE: 23
caggcctcct tgatattttt cctttaaaa                                        29

<210> SEQ ID NO 24
<211> LENGTH: 19
<212> TYPE: DNA
<213> ORGANISM: Artificial Sequence
<220> FEATURE:
<223> OTHER INFORMATION: Probe 1 for Marker CGMMV_5

<400> SEQUENCE: 24
cttagctgaa tcatccttg                                                   19

<210> SEQ ID NO 25
<211> LENGTH: 18
<212> TYPE: DNA
<213> ORGANISM: Artificial Sequence
<220> FEATURE:
<223> OTHER INFORMATION: Probe 2 for Marker CGMMV_5

<400> SEQUENCE: 25
ttagctgaat cgtccttg                                                    18

<210> SEQ ID NO 26
<211> LENGTH: 400
<212> TYPE: DNA
<213> ORGANISM: Artificial Sequence
<220> FEATURE:
<223> OTHER INFORMATION: Nucleotide sequence of Marker CGMMV_6
<220> FEATURE:
<221> NAME/KEY: variation
<222> LOCATION: (212)..(212)
<223> OTHER INFORMATION: Variant at position 212: G

<400> SEQUENCE: 26
tttctgtaac atatctggaa aattaatatg tgaagcgttg ggacaataat gaaaaactaa      60
taaagactgc tgctgtagtg cagtattata gattatgctc tccttctcta tctttcgtga     120
aattctggtg gtggtggatg ctaatttgtt tcagtgcttg tagtttctaa tgttgctatt     180
cttgctttta tcttgctctt caggctttgc cgcccacagc tataaacttt gtgccactga     240
aacaggtaaa atctatcatc cccttagaac gagttttttcc tccttttttat ccgttattaa    300 gtttgaatac aacgagtatt tcagattttc catcaagatc ttgtatgtga actgattctt     360
cttgcattct ttttgcctcc cctccgcctc ttttgaaagt                           400

<210> SEQ ID NO 27
<211> LENGTH: 29
<212> TYPE: DNA
<213> ORGANISM: Artificial Sequence
<220> FEATURE:
<223> OTHER INFORMATION: Forward primer for Marker CGMMV_6
```

```
<400> SEQUENCE: 27
gctattcttg cttttatctt gctcttcag                              29

<210> SEQ ID NO 28
<211> LENGTH: 24
<212> TYPE: DNA
<213> ORGANISM: Artificial Sequence
<220> FEATURE:
<223> OTHER INFORMATION: Reverse primer for Marker CGMMV_6

<400> SEQUENCE: 28
cctgtttcag tggcacaaag ttta                                   24

<210> SEQ ID NO 29
<211> LENGTH: 17
<212> TYPE: DNA
<213> ORGANISM: Artificial Sequence
<220> FEATURE:
<223> OTHER INFORMATION: Probe 1 for Marker CGMMV_6

<400> SEQUENCE: 29
tagctgtggg tggcaaa                                           17

<210> SEQ ID NO 30
<211> LENGTH: 14
<212> TYPE: DNA
<213> ORGANISM: Artificial Sequence
<220> FEATURE:
<223> OTHER INFORMATION: Probe 2 for Marker CGMMV_6

<400> SEQUENCE: 30
ctgtgggcgg caaa                                              14

<210> SEQ ID NO 31
<211> LENGTH: 121
<212> TYPE: DNA
<213> ORGANISM: Artificial Sequence
<220> FEATURE:
<223> OTHER INFORMATION: Nucleotide sequence of Marker CGMMV_7
<220> FEATURE:
<221> NAME/KEY: variation
<222> LOCATION: (61)..(61)
<223> OTHER INFORMATION: variant at position 61:G

<400> SEQUENCE: 31
gtatgaaagc atttgcaaag tgaacgtagt gagacaaatt gatcaatgaa atgttcacaa    60
ggccattact tttgaactta cttctttcaa ctaaaatcac aaggtggata atgtgggggg   120
a                                                                  121

<210> SEQ ID NO 32
<211> LENGTH: 25
<212> TYPE: DNA
<213> ORGANISM: Artificial Sequence
<220> FEATURE:
<223> OTHER INFORMATION: Forward primer for Marker CGMMV_7

<400> SEQUENCE: 32
tgcaaagtga acgtagtgag acaaa                                  25

<210> SEQ ID NO 33
<211> LENGTH: 29
<212> TYPE: DNA
<213> ORGANISM: Artificial Sequence
<220> FEATURE:
```

```
<223> OTHER INFORMATION: Reverse primer for Marker CGMMV_7

<400> SEQUENCE: 33
tccaccttgt gattttagtt gaaagaagt                                    29

<210> SEQ ID NO 34
<211> LENGTH: 19
<212> TYPE: DNA
<213> ORGANISM: Artificial Sequence
<220> FEATURE:
<223> OTHER INFORMATION: Probe 1 for Marker CGMMV_7

<400> SEQUENCE: 34
aaatgttcac aaagccatt                                               19

<210> SEQ ID NO 35
<211> LENGTH: 17
<212> TYPE: DNA
<213> ORGANISM: Artificial Sequence
<220> FEATURE:
<223> OTHER INFORMATION: Probe 2 for Marker CGMMV_7

<400> SEQUENCE: 35
atgttcacaa ggccatt                                                 17

<210> SEQ ID NO 36
<211> LENGTH: 121
<212> TYPE: DNA
<213> ORGANISM: Artificial Sequence
<220> FEATURE:
<223> OTHER INFORMATION: Nucleotide sequence of Marker CGMMV_8
<220> FEATURE:
<221> NAME/KEY: variation
<222> LOCATION: (61)..(61)
<223> OTHER INFORMATION: Variant at position 61:G
<220> FEATURE:
<221> NAME/KEY: misc_feature
<222> LOCATION: (111)..(111)
<223> OTHER INFORMATION: n is a, c, g, or t

<400> SEQUENCE: 36
ggaatccgcc tccaacgtca tatattcttc tccatctcaa tcgtcctttt atttagcttc   60
gtgctaattt gttgagactg atgagttgat tataatgatt aaagtactta nttagctagc  120
t                                                                 121

<210> SEQ ID NO 37
<211> LENGTH: 27
<212> TYPE: DNA
<213> ORGANISM: Artificial Sequence
<220> FEATURE:
<223> OTHER INFORMATION: Forward primer for Marker CGMMV_8

<400> SEQUENCE: 37
cctccaacgt catatattct tctccat                                      27

<210> SEQ ID NO 38
<211> LENGTH: 38
<212> TYPE: DNA
<213> ORGANISM: Artificial Sequence
<220> FEATURE:
<223> OTHER INFORMATION: Reverse primer for Marker CGMMV_8

<400> SEQUENCE: 38
tcgtttacaa gctagctaat taagtacttt aatcatta                          38
```

-continued

```
<210> SEQ ID NO 39
<211> LENGTH: 18
<212> TYPE: DNA
<213> ORGANISM: Artificial Sequence
<220> FEATURE:
<223> OTHER INFORMATION: Probe 1 for Marker CGMMV_8

<400> SEQUENCE: 39
acaaattagc aagaagct                                                    18

<210> SEQ ID NO 40
<211> LENGTH: 18
<212> TYPE: DNA
<213> ORGANISM: Artificial Sequence
<220> FEATURE:
<223> OTHER INFORMATION: Probe 2 for Marker CGMMV_8

<400> SEQUENCE: 40
acaaattagc acgaagct                                                    18

<210> SEQ ID NO 41
<211> LENGTH: 110
<212> TYPE: DNA
<213> ORGANISM: Artificial Sequence
<220> FEATURE:
<223> OTHER INFORMATION: Core sequence of Marker CGMMV_1
<220> FEATURE:
<221> NAME/KEY: misc_feature
<222> LOCATION: (39)..(39)
<223> OTHER INFORMATION: n is a, g, c or t
<220> FEATURE:
<221> NAME/KEY: misc_feature
<222> LOCATION: (92)..(92)
<223> OTHER INFORMATION: n is a, g, c or t

<400> SEQUENCE: 41
cttgaagttt gtcagtctgc atattgttta tatttttcat attaatgcaa aatgttactt      60
gaaacatgag gggcatgttg agatgttgag aatcccacat cgaaaagacc                110

<210> SEQ ID NO 42
<211> LENGTH: 141
<212> TYPE: DNA
<213> ORGANISM: Artificial Sequence
<220> FEATURE:
<223> OTHER INFORMATION: Core sequence of Marker CGMMV_2
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t

<400> SEQUENCE: 42
aggtttggct aacccatatt ttaggggagg tgctgccgan ttttttgtag aattttatat      60
tacttgttct attataagtt taagttgaat antgcttgga ttcaaaaagc gttcttataa    120
cacgatctag gttaggaggg g                                              141

<210> SEQ ID NO 43
<211> LENGTH: 95
<212> TYPE: DNA
<213> ORGANISM: Artificial Sequence
<220> FEATURE:
<223> OTHER INFORMATION: Core sequence of Marker CGMMV_3

<400> SEQUENCE: 43
```

| | |
|---|---|
| ccaattcaag aggtttagaa aagagcatat attaactttc tagtctggga cgcctaatta | 60 |
| tatttcttct aacacactct taatgaacct aggtg | 95 |

<210> SEQ ID NO 44
<211> LENGTH: 82
<212> TYPE: DNA
<213> ORGANISM: Artificial Sequence
<220> FEATURE:
<223> OTHER INFORMATION: Core sequence of Marker CGMMV_4

<400> SEQUENCE: 44

| | |
|---|---|
| gttgttgata tctctgtcgc gaagatctta gcctggaata gtgatcaact ccccatatat | 60 |
| gagcctggtc ttgatgaagt ag | 82 |

<210> SEQ ID NO 45
<211> LENGTH: 92
<212> TYPE: DNA
<213> ORGANISM: Artificial Sequence
<220> FEATURE:
<223> OTHER INFORMATION: Core sequence of Marker CGMMV_5

<400> SEQUENCE: 45

| | |
|---|---|
| ggatgccaga gattgtcaaa cctttcaagg acgattcagc taagcaagaa agatttgagc | 60 |
| agtttttaaa ggaaaaatat caaggaggcc tg | 92 |

<210> SEQ ID NO 46
<211> LENGTH: 66
<212> TYPE: DNA
<213> ORGANISM: Artificial Sequence
<220> FEATURE:
<223> OTHER INFORMATION: Core sequence of Marker CGMMV_6

<400> SEQUENCE: 46

| | |
|---|---|
| gctattcttg cttttatctt gctcttcagg ctttgccgcc cacagctata aactttgtgc | 60 |
| cactga | 66 |

<210> SEQ ID NO 47
<211> LENGTH: 88
<212> TYPE: DNA
<213> ORGANISM: Artificial Sequence
<220> FEATURE:
<223> OTHER INFORMATION: Alternative sequence of Marker CGMMV_7

<400> SEQUENCE: 47

| | |
|---|---|
| ggctcagctt ctgattctga aattgaacgt gagagggaag aaattaaaag gaggaggcag | 60 |
| aaaattatgg ctgagaaagc agcggcca | 88 |

<210> SEQ ID NO 48
<211> LENGTH: 124
<212> TYPE: DNA
<213> ORGANISM: Artificial Sequence
<220> FEATURE:
<223> OTHER INFORMATION: Alternative sequence of Marker CGMMV_8

<400> SEQUENCE: 48

| | |
|---|---|
| ccctgagaaa aatctaaaag ttacccaaaa ttttgatatt ttgaagtgct aggggccatt | 60 |
| tttgtgatgt tgcgtggttt tgaaatgttg tatcgatgta atagaattgg gataacatgt | 120 |
| atgg | 124 |

US 11,807,863 B2

RESISTANCE TO CUCUMBER GREEN MOTTLE MOSAIC VIRUS IN *CUCUMIS SATIVUS*

CROSS-REFERENCE TO RELATED APPLICATIONS

This application claims the priority of U.S. Provisional Appl. Ser. No. 62/989,347, filed Mar. 13, 2020, which is incorporated herein by reference in its entirety.

INCORPORATION OF SEQUENCE LISTING

A sequence listing containing the file named "SEMB044US-revised_ST25.txt," which is 18.4 kilobytes (measured in MS-Windows®) and created on Feb. 22, 2023 and comprising 48 sequences, is incorporated herein by reference in its entirety.

FIELD OF THE INVENTION

The present invention relates to the field of plant breeding, more specifically to methods and compositions for producing cucumber plants exhibiting increased disease resistance to the Cucumber Green Mottle Mosaic Virus (CGMMV).

BACKGROUND OF THE INVENTION

Disease resistance is an important trait in agriculture, particularly for the production of food crops. Although disease resistance alleles have been identified in cucumber plants, efforts to introduce these alleles into elite lines are hindered by a lack of specific markers linked to the alleles, linkage drag that leads to unacceptable plant quality, and a lack of high levels of resistance. The use of marker-assisted selection (MAS) in plant breeding methods has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, epistasis and an often incomplete understanding of the genetic background underlying expression of a desired phenotype.

SUMMARY OF THE INVENTION

The present invention provides an agronomically elite *Cucumis sativus* plant comprising a recombinant chromosomal segment on chromosome 1 and a recombinant chromosomal segment on chromosome 5, wherein said recombinant chromosomal segment on chromosome 5 confers increased resistance to Cucumber Green Mottle Mosaic Virus (CGMMV) relative to a *Cucumis sativus* plant that lacks said recombinant chromosomal segment, and wherein said recombinant chromosomal segment on chromosome 1 confers increased resistance to CGMMV in a *Cucumis sativus* plant that comprises said recombinant chromosomal segment on chromosome 5 relative to a *Cucumis sativus* plant that comprises the recombinant chromosomal segment on chromosome 5 and lacks said recombinant chromosomal segment on chromosome 1. In some embodiments, said recombinant chromosomal segment on chromosome 1 comprises a marker locus selected from the group consisting of: marker locus CGMMV_M4 (SEQ ID NO: 16), marker locus CGMMV_M5 (SEQ ID NO: 21), and marker locus CGMMV_M6 (SEQ ID NO: 26). In other embodiments, said recombinant chromosomal segment on chromosome 5 comprises a marker locus selected from the group consisting of: marker locus CGMMV_M1 (SEQ ID NO: 1), marker locus CGMMV_M2 (SEQ ID NO: 6), and marker locus CGMMV_M3 (SEQ ID NO: 11). In certain embodiments, said recombinant chromosomal segment on chromosome 1 or said recombinant chromosomal segment on chromosome 5 comprises an allele conferring said increased resistance to CGMMV that is obtainable from *Cucumis sativus* accession Cornell Chinese Long, a representative sample of seed of said accession having been deposited under ATCC Accession No. PTA-126674. In some embodiments, said recombinant chromosomal segment on chromosome 1 that confers resistance to CGMMV is located between 1,723,554 bp and 2,141,985 bp on chromosome 1 of the public cucumber genome v2 map and wherein said recombinant chromosomal segment on chromosome 5 that confers resistance to CGMMV is located between 5,704,478 bp and 6,345,266 bp on chromosome 5 of the public cucumber genome v2 map. In other embodiments, said recombinant chromosomal segment on chromosome 1 lacks a deleterious allele genetically linked thereto confers to the plant a leaf vein necrosis phenotype when present. In yet other embodiments, said recombinant chromosomal segment on chromosome 1 lacks a donor plant allele at marker locus CGMMV_M7 (SEQ ID NO: 31) or marker locus CGMMV_M8 (SEQ ID NO: 36). In further embodiments, said plant is defined as an inbred or hybrid plant.

The present invention additionally provides a seed that produces an agronomically elite *Cucumis sativus* plant comprising a recombinant chromosomal segment on chromosome 1 and a recombinant chromosomal segment on chromosome 5, wherein said recombinant chromosomal segment on chromosome 5 confers increased resistance to Cucumber Green Mottle Mosaic Virus (CGMMV) relative to a *Cucumis sativus* plant that lacks said recombinant chromosomal segment, and wherein said recombinant chromosomal segment on chromosome 1 confers increased resistance to CGMMV in a *Cucumis sativus* plant that comprises said recombinant chromosomal segment on chromosome 5 relative to a *Cucumis sativus* plant that comprises the recombinant chromosomal segment on chromosome 5 and lacks said recombinant chromosomal segment on chromosome 1. In some embodiments, the invention provides a plant part of an agronomically elite *Cucumis sativus* plant comprising a recombinant chromosomal segment on chromosome 1 and a recombinant chromosomal segment on chromosome 5, wherein said recombinant chromosomal segment on chromosome 5 confers increased resistance to Cucumber Green Mottle Mosaic Virus (CGMMV) relative to a *Cucumis sativus* plant that lacks said recombinant chromosomal segment, and wherein said recombinant chromosomal segment on chromosome 1 confers increased resistance to CGMMV in a *Cucumis sativus* plant that comprises said recombinant chromosomal segment on chromosome 5 relative to a *Cucumis sativus* plant that comprises the recombinant chromosomal segment on chromosome 5 and lacks said recombinant chromosomal segment on chromosome 1. In certain embodiments, the plant part is selected from a stem, petiole, cotyledon, flower, anther, pollen, ovary, root, root tip, protoplast, ovule, shoot, embryo, embryo sac, bud, leaf, meristem or cell.

The present invention provides a recombinant DNA segment from *Cucumis sativus* chromosome 1 comprising a Cucumber Green Mottle Mosaic Virus (CGMMV) resistance allele that confers increased resistance to CGMMV and lacks a deleterious allele genetically linked thereto that confers a leaf vein necrosis phenotype when present, wherein said increased resistance is exhibited in a *Cucumis sativus* plant comprising a recombinant chromosomal segment on chromosome 5 that confers increased resistance to CGMMV relative to a plant that comprises the recombinant chromosomal segment on chromosome 5 and lacks the recombinant DNA segment on chromosome 1. In some embodiments, said CGMMV resistance allele is derived from a plant of *Cucumis sativus* accession Cornell Chinese Long, a representative sample of seed of said accession having been deposited under ATCC Accession No. PTA-126674. In other embodiments, said recombinant DNA segment comprises a sequence selected from the group consisting of SEQ ID NOs: 16, 21, 26, 31, and 36. In further embodiments, said recombinant DNA segment is further defined as comprised within a plant, plant part, plant cell, or seed.

The present invention provides a method for producing an elite *Cucumis sativus* plant with improved Cucumber Green Mottle Mosaic Virus (CGMMV) resistance comprising introgressing into said plant at least one CGMMV resistance allele within a chromosomal segment flanked in the genome of said plant by: (a) marker locus CGMMV_M1 (SEQ ID NO: 1) and marker locus CGMMV_M2 (SEQ ID NO: 11) on chromosome 5; or (b) marker locus CGMMV_M4 (SEQ ID NO: 16) and marker locus CGMMV_M5 (SEQ ID NO: 21) on chromosome 1, wherein said introgressing comprises marker-assisted selection or wherein the introgressing comprises introgressing said chromosomal segment on chromosome 1. In some embodiments, said introgressing comprises: crossing a plant comprising said chromosomal segment with itself or with a second *Cucumis sativus* plant of a different genotype to produce at least a first progeny plant; and selecting a progeny plant comprising said chromosomal segment. In other embodiments, said introgressing comprises backcrossing or assaying for said CGMMV resistance. In yet other embodiments, said marker-assisted selection comprises detecting a marker locus genetically linked to said CGMMV resistance allele selected from the group consisting of: marker locus CGMMV_M1 (SEQ ID NO: 1), marker locus CGMMV_M2 (SEQ ID NO: 6), marker locus CGMMV_M3 (SEQ ID NO: 11), marker locus CGMMV_M4 (SEQ ID NO: 16), marker locus CGMMV_M5 (SEQ ID NO: 21), and marker locus CGMMV_M6 (SEQ ID NO: 26). In further embodiments, said progeny plant is an $F_2$-$F_6$ progeny plant. In other embodiments, said chromosomal segment on chromosome 1 lacks a deleterious allele genetically linked thereto that confers leaf vein necrosis when present. The invention further provides *Cucumis sativus* plants obtainable by the methods provided herein.

The present invention also provides a method for identifying a *Cucumis sativus* plant comprising a Cucumber Green Mottle Mosaic Virus (CGMMV) resistance allele: a) obtaining nucleic acids from at least a first *Cucumis sativus* plant; and b) identifying in said nucleic acids the presence of at least a first genetic marker indicative of the presence of a chromosomal segment flanked in the genome of said plant by: (i) marker locus CGMMV_M1 (SEQ ID NO: 1) and marker locus CGMMV_M2 (SEQ ID NO: 11) on chromosome 5; or (ii) marker locus CGMMV_M4 (SEQ ID NO: 16) and marker locus CGMMV_M5 (SEQ ID NO: 21) on chromosome 1, wherein said chromosomal segment on chromosome 5 confers increased resistance to CGMMV relative to a *Cucumis sativus* plant that lacks said chromosomal segment on chromosome 5, and wherein said chromosomal segment on chromosome 1 confers increased resistance to CGMMV in a *Cucumis sativus* plant that comprises said recombinant chromosomal segment on chromosome 5 relative to a *Cucumis sativus* plant that comprises the recombinant chromosomal segment on chromosome 5 and lacks the recombinant chromosomal segment on chromosome 1. In some embodiments, said identifying comprises detecting a marker genetically linked to marker locus CGMMV_M1 (SEQ ID NO: 1), marker locus CGMMV_M2 (SEQ ID NO: 6), marker locus CGMMV_M3 (SEQ ID NO: 11), marker locus CGMMV_M4 (SEQ ID NO: 16), marker locus CGMMV_M5 (SEQ ID NO: 21), or marker locus CGMMV_M6 (SEQ ID NO: 26).

DETAILED DESCRIPTION

Figure 1:
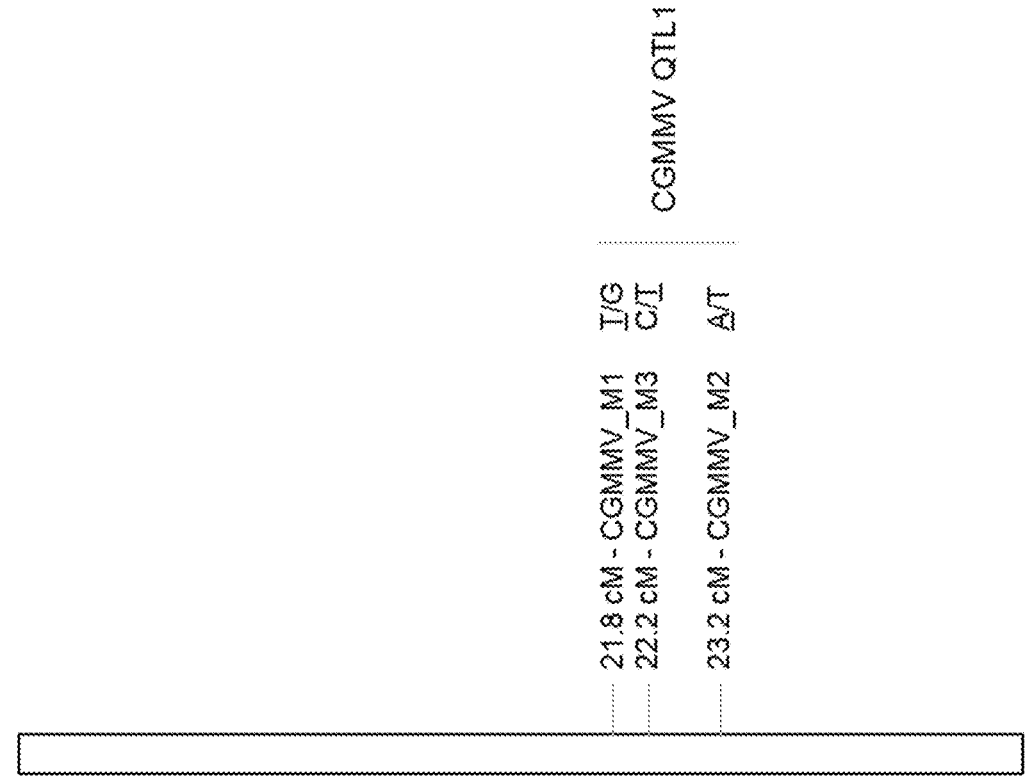
FIG. 1: Shows a diagram of the marker positions related to CGMMV resistance QTL region on chromosome 5 and of the CGMMV resistance-enhancing and leaf vein necrosis QTLSs on chromosome 1. The nucleotide changes are indicated next to the marker. The underlined nucleotide is the favorable allele.
Figure 1:
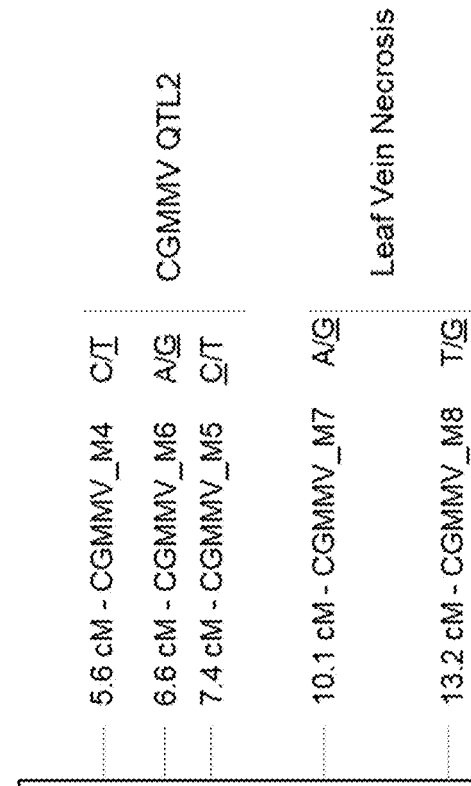

Cucumber (*Cucumis sativus*) is a widely cultivated plant in the gourd family, Cucurbitaceae. It is a creeping vine that bears cucumiform fruits that are used as vegetables. There are three main varieties of cucumber: slicing, pickling, and seedless. The fruit of typical cultivars of cucumber is roughly cylindrical, but elongated with tapered ends, and may be as large as 60 centimeters long and 10 centimeters in diameter.

One of the most damaging plant viruses to affect commercial cucumber crops is Cucumber green mottle mosaic virus (CGMMV), which can cause disease in all domesticated cucurbitaceous crops. CGMMV is a Tobamovirus of the Virgaviridae family and generally causes systemic mottle and mosaic symptoms on the leaves of cucurbits. In cucumber, both the leaves and fruit can show symptoms depending on the severity of the infection. Infections in the leaves leads to a reduction in plant performance and yield. In severe cases, the fruit are also affected, having scalded skin and growth deformations that render them unmarketable. CGMMV transmits easily through seed and pollen and through mechanical means, e.g. workers in the greenhouse/field. The lack of effective crop protection and seed treatments to remove the virus has led to its worldwide spread. In the absence of effective treatments, cucumber breeders rely on early monitoring, awareness of the disease, and quarantine measures to prevent spread/infection of the virus. Despite fastidious implementation of such methods for control, success of containing the virus is not guaranteed. The only effective means to prevent CGMMV spreading through a cucumber crop is through development of virus resistant plants. No *Cucumis sativus* cultivars are currently available in the market that demonstrate an effective resistance to CGMMV.

Full resistance to CGMMV is preferable to breeders, as this enables the replication and spread of the virus, along with symptom development, to be restricted. Given the unavailability of such resistance in *Cucumis sativus* cultivars, plants that are tolerant have been accepted by cucumber growers, as these do not show the adverse effects on yield and fruit deformation upon infection. However, current commercial varieties only show a partial reduction in symptoms. There still exists a need to identify further resistance genes, introgression fragments or QTLs conferring increased resistance against CGMMV and sources from which such resistance genes, introgression fragments or QTLs can be identified, introduced and/or used in *Cucumis sativus*.

Crespo et al. (*Euphytica* 214:201-211; 2018) screened germplasm accessions of *Cucumis sativus*, as well as *Cucumis anguria* and *Cucumis metuliferus*, by infecting plants with CGMMV and evaluating levels of resistance, based on symptom severity and viral loads determined through RT-RCR. Severe symptoms were observed following inoculation in *Cucumis metuliferus* and in 44 *Cucumis sativus* accessions. Ten *Cucumis sativus* accession showed intermediate symptoms and only two *Cucumis sativus* accessions showed mild symptoms. The genetic basis of this resistance is not known.

The present inventors have made significant advancements in obtaining CGMMV resistance in cucumber by identifying a novel QTL on chromosome 1 which can be combined with a QTL on chromosome 5 to increase CGMMV resistance and by developing novel recombinant chromosomal segments on chromosome 5 and chromosome 1, particularly recombinant chromosomal segments on chromosome 1 that lack a deleterious allele causing leaf vein necrosis, which is normally genetically linked to the CGMMV resistance-enhancing allele. In addition, novel markers for the introgressed alleles are provided, allowing the alleles to be accurately introgressed and tracked during plant breeding. As such, the invention permits introgression of the virus resistance alleles into any desired cucumber genotype.

In certain embodiments, cucumber plants are provided comprising an introgressed CGMMV resistance allele on chromosome 5, wherein the allele confers to the plant increased resistance to CGMMV compared to a plant not comprising the allele. In addition, plants are provided comprising an additional introgressed CGMMV resistance allele on chromosome 1, wherein the allele confers to the plant increased resistance to CGMMV compared to a plant not comprising the allele or compared to a plant only comprising the resistance allele on chromosome 5.

In some embodiments, the introgressed CGMMV resistance allele is defined as located on chromosome 5 within a recombinant chromosomal segment flanked by marker locus CGMMV_M1 (SEQ ID NO: 1) and marker locus CGMMV_M2 (SEQ ID NO: 6). The invention further provides marker locus CGMMV_M3 (SEQ ID NO: 11) as an interstitial marker between markers CGMMV_M1 and CGMMV_M2 that can be used to select the introgressed CGMMV resistance allele on chromosome 5. Marker locus CGMMV_M1 comprises a SNP change from T to G at 5,704,478 bp of chromosome 5 of the public cucumber genome v2 map. Marker locus CGMMV_M2 comprises a SNP change from A to T at 6,345,266 bp of chromosome 5 of the public cucumber genome v2 map. Marker locus CGMMV_M3 comprises a SNP change from C to T at 5,889,044 bp of chromosome 5 of the public cucumber genome v2 map. The SNP changes and locations on the public cucumber genome v2 map for the markers are also indicated in Table 1.

In some embodiments, the additional introgressed CGMMV resistance allele is defined as located on chromosome 1 within a recombinant chromosomal segment flanked by marker locus CGMMV_M4 (SEQ ID NO: 16) and marker locus CGMMV_M5 (SEQ ID NO: 21). The invention further provides marker locus CGMMV_M6 (SEQ ID NO: 26) as an interstitial marker between markers CGMMV_M4 and CGMMV_M5 that can be used to select the introgressed CGMMV resistance allele on chromosome 1. Marker locus CGMMV_M4 comprises a SNP change from C to T at 1,723,554 bp of chromosome 1 of the public cucumber genome v2 map. Marker locus CGMMV_M5 comprises a SNP change from C to T at 2,141,985 bp of chromosome 1 of the public cucumber genome v2 map. Marker locus CGMMV_M6 comprises a SNP change from A to G at 1,926,358 bp of chromosome 1 of the public cucumber genome v2 map. The SNP changes and locations on the public cucumber genome v2 map for the markers are also indicated in Table 2.

In some embodiments, the recombinant chromosomal segment is defined comprising a CGMMV resistance allele located on chromosome 1 but lacking a genetically linked allele conferring leaf vein necrosis. The invention provides marker loci CGMMV_M7 (SEQ ID NO: 31) and CGMMV_M8 (SEQ ID NO: 36) which can be used to define a recombinant chromosomal segment on chromosome 1 conferring increased resistance to CGMMV without causing leaf vein necrosis in the plant. The SNP changes and locations on the public cucumber genome v2 map for these markers are also indicated in Table 2.

The public genome of cucumber is available at, for example at cucurbitgenomics.org, (CuGenDB) and one skilled in the art would understand how to locate the marker sequences provided for the first time in the instant application on any version (or later version) of the public genome.

In other embodiments, the invention provides plants comprising one or more of the novel recombinant introgressions provided herein. These novel recombinant introgressions confer increased resistance to CGMMV in cucumber plants compared to plants which are genetically similar except for the absence of the novel recombinant introgressions. Methods of producing the plants described herein are further provided. The invention further provides novel trait-linked markers that can be used to produce plants comprising novel recombinant introgressions on chromosomes 1 and 5 that confer CGMMV resistance as described herein. In particular embodiments, the invention provides the markers shown in Tables 1 and 2, which have been shown herein to be genetically linked to CGMMV resistance in plants.

Methods of producing plants comprising the introgressed introgressions described herein are further provided. In some examples, donor DNA from a resistant donor parent is introgressed into a cultivated plant line (the recurrent parent line). CGMMV_M1 (SEQ ID NO: 1) or CGMMV_M2 (SEQ ID NO: 6) can be used to select the allele of the recurrent parent and CGMMV_M3 (SEQ ID NO: 11) can be used to select the allele of the resistance donor parent on chromosome 5. Likewise, CGMMV_M4 (SEQ ID NO: 16) or CGMMV_M5 (SEQ ID NO: 21) can be used to select the allele of the recurrent parent and CGMMV_M6 (SEQ ID NO: 26) can be used to select the allele of the resistance donor parent on chromosome 1.

In certain embodiments, the invention provides methods of producing or selecting a cucumber plant exhibiting resistance to CGMMV comprising: a) crossing a cucumber plant provided herein with itself or with a second cucumber plant of a different genotype to produce one or more progeny plants; and b) selecting a progeny plant comprising the first introgressed allele and/or the second introgressed allele. In some embodiments, methods of the invention comprise selecting a progeny plant by detecting nucleic acids comprising marker locus CGMMV_M1 (SEQ ID NO: 1), CGMMV_M2 (SEQ ID NO: 6) or CGMMV_M3 (SEQ ID NO: 11) and/or CGMMV_M4 (SEQ ID NO: 16), CGMMV_M5 (SEQ ID NO: 21), or CGMMV_M6 (SEQ ID NO: 26).

Because genetically diverse plant lines can be difficult to cross, the introgression of CGMMV resistance alleles into cultivated lines using conventional breeding methods could require prohibitively large segregating populations for progeny screens with an uncertain outcome. Marker-assisted selection (MAS) is therefore essential for the effective introgression of CGMMV resistance alleles into elite cultivars. However, previously known markers for CGMMV resistance have failed to discriminate between donor DNA conferring virus resistance and donor DNA conferring deleterious traits. This has been further complicated by the previous inability to resolve the specific regions associated with virus resistance. For the first time, the present invention enables effective MAS by providing improved and validated markers for detecting genotypes associated with virus resistance without the need to grow large populations of plants to maturity in order to observe the phenotype.

It should be remarked that the current document refers to the markers shown in Tables 1 and 2, and that whenever reference is made to particular marker nucleotide sequence, this also includes a reference to the corresponding core nucleotide sequence of the marker and to a sequence substantially identical to such nucleotide sequences.

I. GENOMIC REGIONS, ALLELES, AND POLYMORPHISMS ASSOCIATED WITH CGMMV RESISTANCE IN CUCUMBER

The invention provides novel introgressions of one or more alleles associated with CGMMV virus resistance in cucumber, together with polymorphic nucleic acids and linked markers for tracking the introgressions during plant breeding.

Non-commercial (non-elite) *Cucumis sativus* varieties exhibiting CGMMV resistance are known in the art and may be used together with the novel trait-linked markers provided herein in accordance with certain embodiments of the invention. For example, wild cucumber accession ‘Cornell Chinese Long’, which also carries the designations PI 267744 and G 2564, can be used as source for CGMMV resistance. This line is available at the U.S. National Plant Germplasm System. Commercial varieties known to be tolerant to CGMMV may also be used as a donor for the locus on chromosome 5. Such examples are Bonbon RZ F1 (24-185), Boncanale RZ F1 (24-223), Bonifacio RZ F1 (24-218), Bonprima RZ F1 (24-243), Bonsanna RZ F1 (24-284), Dee Host, Garpo, Getty, Gotja, Hi Pace, Shakira, and Verdon RZ F1 (24-150).

Using the improved genetic markers and assays of the invention, the present inventors were able to successfully identify novel reduced introgressions that confer CGMMV resistance to commercially cultivated (elite) cucumber plants (including varieties). In certain embodiments, the invention provides cucumber plants comprising donor DNA between marker locus CGMMV_M1 (SEQ ID NO: 1) and marker locus CGMMV_M2 (SEQ ID NO: 6) on chromosome 5, and/or marker locus CGMMV_M4 (SEQ ID NO: 16) and marker locus CGMMV_M5 (SEQ ID NO: 21) on chromosome 1. Preferably, the donor DNA on chromosome 1 lacks the donor DNA between markers CGMMV_M7 (SEQ ID NO: 31) and CGMMV_M8 (SEQ ID NO: 36) associated with a leaf vein necrosis phenotype.

To the extent required, the elite cucumber varieties encompassed by this invention do not encompass wild cucumber varieties exhibiting CGMMV resistance. Thus, the cucumber varieties of the invention comprise elite cucumber varieties comprising the mentioned recombinant chromosomal segments, provided they are not wild cucumber accessions exhibiting CGMMV resistance such as Cornell Chinese Long.

The novel introgressions provided herein confer robust resistance to CGMMV. The invention therefore represents a significant advance in the art.

II. INTROGRESSION OF GENOMIC REGIONS ASSOCIATED WITH CGMMV RESISTANCE

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel accurate markers for identifying and tracking introgression of one or more of the genomic regions disclosed herein from a CGMMV resistant plant into a cultivated line. The invention further provides markers for identifying and tracking the novel introgressions disclosed herein during plant breeding, including the markers set forth in Table 1 or Table 2.

Markers within or linked to any of the genomic intervals of the present invention may be useful in a variety of breeding efforts that include introgression of genomic regions associated with disease resistance into a desired genetic background. For example, a marker within 40 cM, 20 cM, 15 cM, 10 cM, 5 cM, 2 cM, or 1 cM of a marker associated with virus or disease resistance described herein can be used for marker-assisted introgression of genomic regions associated with a virus resistant phenotype.

Cucumber plants comprising one or more introgressed regions associated with a desired phenotype wherein at least 10%, 25%, 50%, 75%, 90%, or 99% of the remaining genomic sequences carry markers characteristic of the recurrent parent germplasm are also provided. Cucumber plants comprising an introgressed region comprising regions closely linked to or adjacent to the genomic regions and markers provided herein and associated with a virus resistance phenotype are also provided.

III. DEVELOPMENT OF VIRUS RESISTANT CUCUMBER VARIETIES

For most breeding objectives, commercial breeders work with germplasm that is “cultivated,” “cultivated type,” or “elite.” These cultivated lines may be used as recurrent parents or as a source of recurrent parent alleles during breeding. Cultivated or elite germplasm is easier to breed because it generally performs well when evaluated for horticultural performance. Many cultivated cucumber types have been developed and are known in the art as being agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. Non-cultivated germplasm may be used as a source of donor alleles during breeding. However, this approach generally presents significant difficulties due to fertility problems associated with crosses between diverse lines, and genetically linked deleterious alleles from the non-cultivated parent. For example, non-cultivated cucumber types can provide alleles associated with disease resistance. However, these non-cultivated types may have poor horticultural qualities such as poor quality, poor architecture, low yield, or small fruit size.

The process of introgressing desirable resistance genes from non-cultivated lines into elite cultivated lines while avoiding problems with genetically linked deleterious alleles or low heritability is a long and often arduous process. In deploying alleles derived from wild relatives it is often desirable to introduce a minimal or truncated introgression that provides the desired trait but lacks detrimental effects. To aid introgression reliable marker assays are preferable to phenotypic screens. Success is furthered by simplifying genetics for key attributes to allow focus on genetic gain for quantitative traits such as disease resistance. Moreover, the process of introgressing genomic regions from non-cultivated lines can be greatly facilitated by the availability of accurate markers for MAS.

One of skill in the art would therefore understand that the alleles, polymorphisms, and markers provided by the invention allow the tracking and introduction of any of the genomic regions identified herein into any genetic background. In addition, the genomic regions associated with virus resistance disclosed herein can be introgressed from one genotype to another and tracked using MAS. Thus, the inventors' discovery of accurate markers associated with virus resistance will facilitate the development of cucumber plants having beneficial phenotypes. For example, seed can be genotyped using the markers of the present invention to select for plants comprising desired genomic regions associated with virus resistance, especially those devoid of leaf vein necrosis. Moreover, MAS allows identification of plants homozygous or heterozygous for a desired introgression.

Inter-species crosses can also result in suppressed recombination and plants with low fertility or fecundity. For example, suppressed recombination has been observed for the tomato nematode resistance gene Mi, the M1a and M1g genes in barley, the Yr17 and Lr20 genes in wheat, the Run1 gene in grapevine, and the Rma gene in peanut. Meiotic recombination is essential for classical breeding because it enables the transfer of favorable alleles across genetic backgrounds, the removal of deleterious genomic fragments, and pyramiding traits that are genetically tightly linked. Therefore, suppressed recombination forces breeders to enlarge segregating populations for progeny screens in order to arrive at the desired genetic combination.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among cucumber species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

IV. MARKER ASSISTED BREEDING AND GENETIC ENGINEERING TECHNIQUES

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita et al. (1989) *Genomics*, 8(2), 271-278), denaturing gradient gel electrophoresis (Myers (1985) EP 0273085), or cleavage fragment length polymorphisms (Life Technologies, Inc., Gaithersburg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer et al. (1992) *Biotechniques* 12(1), 82-87), or PCR amplification of multiple specific alleles (PAMSA; Dutton and Sommer (1991) *Biotechniques*, 11(6), 700-7002).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a cucumber plant a genotype associated with disease resistance, identify a cucumber plant with a genotype associated with virus resistance, and to select a cucumber plant with a genotype associated with virus resistance. In certain embodiments of methods of the invention, polymorphic nucleic acids can be used to produce a cucumber plant that comprises in its genome an introgressed locus associated with virus resistance. In certain embodiments of the invention, polymorphic nucleic acids can be used to breed progeny cucumber plants comprising a locus or loci associated with virus resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to a condition where the two alleles at a locus are different.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with virus resistance in cucumber plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. (1986) Cold Spring Harbor Symp. *Quant. Biol.* 51:263-273; European Patent 50,424; European Patent 84,796; European Patent 258,017; European Patent 237,362; European Patent No. 201,184; U.S. Pat. Nos. 4,683,202; 4,582,788; and 4,683, 194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613; 5,217,863; 5,210,015; 5,876,930; 6,030, 787; 6,004,744; 6,013,431; 5,595,890; 5,762,876; 5,945, 283; 5,468,613; 6,090,558; 5,800,944; 5,616,464; 7,312, 039; 7,238,476; 7,297,485; 7,282,355; 7,270,981 and 7,250, 252 all of which are incorporated herein by reference in their entirety. However, the compositions and methods of the present invention can be used in conjunction with any polymorphism typing method to detect polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523 (2003); Cui et al., *Bioinformatics* 21:3852-3858 (2005)). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is described in U.S. Pat. Nos. 6,799,122; 6,913,879; and 6,996, 476.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

Various genetic engineering technologies have been developed and may be used by those of skill in the art to introduce traits in plants. In certain aspects of the claimed invention, traits are introduced into cucumber plants via altering or introducing a single genetic locus or transgene into the genome of a variety or progenitor thereof. Methods of genetic engineering to modify, delete, or insert genes and polynucleotides into the genomic DNA of plants are well-known in the art.

In specific embodiments of the invention, improved cucumber lines can be created through the site-specific modification of a plant genome. Methods of genetic engineering include, for example, utilizing sequence-specific nucleases such as zinc-finger nucleases (see, for example, U.S. Patent Appl. Pub. No. 2011/0203012); engineered or native meganucleases; TALE-endonucleases (see, for example, U.S. Pat. Nos. 8,586,363 and 9,181,535); and RNA-guided endonucleases, such as those of the CRISPR/Cas systems (see, for example, U.S. Pat. Nos. 8,697,359 and 8,771,945 and U.S. Patent Appl. Pub. No. 2014/0068797). One embodiment of the invention thus relates to utilizing a nuclease or any associated protein to carry out genome modification. This nuclease could be provided heterologously within donor template DNA for templated-genomic editing or in a separate molecule or vector. An introgressed DNA construct may also comprise a sequence encoding one or more guide RNAs to direct the nuclease to the site within the plant genome to be modified. Further methods for altering or introducing a single genetic locus include, for example, utilizing single-stranded oligonucleotides to introduce base pair modifications in a plant genome (see, for example Sauer et al., *Plant Physiol,* 170(4):1917-1928, 2016).

Methods for site-directed alteration or introduction of a single genetic locus are well-known in the art and include those that utilize sequence-specific nucleases, such as the aforementioned, or complexes of proteins and guide-RNA that cut genomic DNA to produce a double-strand break (DSB) or nick at a genetic locus. As is well-understood in the art, during the process of repairing the DSB or nick introduced by the nuclease enzyme, a donor template, transgene, or expression cassette polynucleotide may become integrated into the genome at the site of the DSB or nick. The presence of homology arms in the DNA to be integrated may promote the adoption and targeting of the insertion sequence into the plant genome during the repair process through homologous recombination or non-homologous end joining (NHEJ).

In another embodiment of the invention, genetic transformation may be used to insert a selected transgene into a plant of the invention or may, alternatively, be used for the preparation of transgenes which can be introduced by backcrossing. Methods for the transformation of plants that are well-known to those of skill in the art and applicable to many crop species include, but are not limited to, electroporation, microprojectile bombardment, *Agrobacterium*-mediated transformation, and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Nat. Biotechnol.,* 3(7):637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Nat. Biotechnol.,* 3:629-635, 1985; U.S. Pat. No. 5,563,055).

Transformation of plant protoplasts also can be achieved using methods based on calcium phosphate precipitation, polyethylene glycol treatment, electroporation, and combinations of these treatments (see, for example, Potrykus et al., *Mol. Gen. Genet.,* 199:183-188, 1985; Omirulleh et al., *Plant Mol. Biol.,* 21(3):415-428, 1993; Fromm et al., *Nature,* 312:791-793, 1986; Uchimiya et al., *Mol. Gen. Genet.,* 204:204, 1986; Marcotte et al., *Nature,* 335:454, 1988). Transformation of plants and expression of foreign genetic elements is exemplified in Choi et al. (*Plant Cell Rep.,* 13:344-348, 1994), and Ellul et al. (*Theor. Appl. Genet.,* 107:462-469, 2003).

V. DEFINITIONS

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which cucumber plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "quantitative trait locus" (QTL) is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any variety that has resulted from breeding and selection for superior agronomic performance. An "elite plant" refers to a plant belonging to an elite variety. Numerous elite varieties are available and known to those of skill in the art of cucumber breeding. An "elite population" is an assortment of elite individuals or varieties that can be used to represent the state of the art in terms of agronomically superior genotypes of a given crop species, such as cucumber. Similarly, an "elite germplasm" or elite strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the terms "recombinant" or "recombined" in the context of a chromosomal segment refer to recombinant DNA sequences comprising one or more genetic loci in a configuration in which they are not found in nature, for example as a result of a recombination event between homologous chromosomes during meiosis.

As used herein, the term "linked," when used in the context of nucleic acid markers and/or genomic regions, means that the markers and/or genomic regions are located on the same linkage group or chromosome such that they tend to segregate together at meiosis.

As used herein "resistance" or "improved resistance" in a plant to disease or virus conditions is an indication that the plant is more able to reduce disease burden than a non-resistant or less resistant plant. Resistance is a relative term, indicating that a "resistant" plant is more able to reduce disease burden or virus burden compared to a different (less resistant) plant (e.g., a different plant variety) grown in similar disease conditions or virus pressure. One of skill will appreciate that plant resistance to disease conditions or virus infestation varies widely, and can represent a spectrum of more-resistant or less-resistant phenotypes. However, by simple observation, one of skill can generally determine the relative resistance of different plants, plant varieties, or plant families under disease conditions or pest pressure, and furthermore, will also recognize the phenotypic gradations of "resistant."

As used herein, "resistance allele" means the nucleic acid sequence associated with tolerance or resistance to a virus.

As used herein, "CGMMV resistance" or "CGMMV resistant plants" are plants that show reduced levels of disease symptoms or no disease symptoms, but in which CGMMV virus particles can readily be detected. CGMMV resistance in cucumber plants thus refers to what in the field of pathology and plant breeding is also known as "symptomless carrier". This type of resistance is can also be referred to as disease tolerance. In this application the terms tolerance and resistance are used interchangeably because currently the only form of resistance to CGMMV in cucumber available to plant breeders takes the form of symptomless carriers.

"Sequence identity" and "sequence similarity" can be determined by alignment of r two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters) share at least a certain minimal percentage of sequence identity. These programs use the Needleman and Wunsch global alignment algorithm to align two sequences over their entire length, maximizing the number of matches and minimizing the number of gaps. Generally, the default parameters are used, with a gap creation penalty=10 and gap extension penalty=0.5 (both for nucleotide and protein alignments). For nucleotides the default scoring matrix used is DNAFULL (Henikoff & Henikoff, 1992, PNAS 89, 10915-10919). Sequence alignments and scores for percentage sequence identity may for example be determined using computer programs, such as EMBOSS, as available on the world wide web under ebi-.ac.uk/Tools/psa/emboss_needle/. Alternatively, sequence similarity or identity may be determined by searching against databases such as FASTA, BLAST, etc., but hits should be retrieved and aligned pairwise to compare sequence identity. Two nucleic acid sequences have "substantial sequence identity" if the percentage sequence identity is at least 85%, 90%, 95%, 98%, 99% or more (e.g. at least 99.1, 99.2 99.3 99.4, 99.5, 99.6, 99.7, 99.8, 99.9 or more (as determined by Emboss "needle" using default parameters, i.e. gap creation penalty=10, gap extension penalty=0.5, using scoring matrix DNAFULL for nucleic acids). Markers may sometimes exhibit variation, particularly in regions which are not recognized by the probes.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

VI. DEPOSIT INFORMATION

A deposit was made of at least 625 seeds of 'Cornell Chinese Long' as described herein. The deposit was made with the American Type Culture Collection (ATCC), 10801 University Boulevard, Manassas, Va. 20110-2209 USA. The deposit is assigned ATCC Accession No. PTA-126674, and the date of deposit was Feb. 25, 2020. Access to the deposit will be available during the pendency of the application to persons entitled thereto upon request. The deposit will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

EXAMPLES

Example 1. CGMMV Resistance Evaluation Assays

Resistance to CGMMV can be tested in cucumber seedlings and in adult plants. The following method is a cucumber seedling test.

CGMMV is maintained on susceptible cucumber plants. Young infected leaves can be stored at −20° C. or at −80° C. without losing virus pathogenicity. To prepare inoculum for an experiment, water and carborundum powder is added to leaf material and subsequently crushed using a mortar and pestle or blender. Water is then added to the crushed leaf material in a 1 (leaf material) to 2.5 (water) w/v ratio. For every 100 ml of water added, 2 teaspoons of carborundum powder is also added to the mix. An experiment should be designed using a randomized complete block design with at least three replicates and at least four (preferably 8) plants per genotype in a replicate. In addition, a control set that is mock-inoculated, i.e. with water and carborundum mix only, should be included. The negative control, i.e. susceptible check, can be any cucumber variety that is susceptible to CGMMV, such as Corona. Controls with intermediate levels of resistance are Shakira, Bonbon, Verdon, or any other variety known to have intermediate resistance levels. As a positive control, i.e. resistant/symptomless carrier, the wild cucumber accession Cornell Chinese Long, available at the USDA under PI 267744) or the seed deposit as disclosed herein, can be used. The plants should be sown in an environment with 26° C. day/night rhythm. The seeds can be sown in, for example, Rockwool plugs, but other substrates may also be used. The seedlings should be inoculated when the cotyledons have fully developed, which is about 7 days after sowing. To inoculate, both cotyledons of each seedling should be rubbed 4 times with a small sponge drenched in the inoculum. The sponge should be replenished at least after inoculating 2 seedlings. In addition, the inoculum should be well mixed when replenishing the sponge, as the carborundum powder has a tendency to sink to the bottom. After inoculation, the plants should be kept in an environment with a 21° C. day/night rhythm, 60-80% humidity, at least 14 hours of light per day. It is possible to treat the plants against mildew infections, but sulfur should not be applied during the trial.

The control plants are checked for symptoms 14 days post inoculation (dpi) to see if these plants are responding as expected. Subsequently, three observations are done for all plants in the experiment. These observations are at 17 dpi, 19 dpi and 21 dpi. A 1-9 rating scale can be used with the following ratings: 1) no virus symptoms on young leaves (i.e. the developing two leaves in the apex/top/canopy of the plant); 2) no symptoms, but a growth reduction compared to non-inoculated control; 3) isolated, yellow spots on young leaves; 4) multiple yellow spots on young leaves; 5) mild, localized mosaic on young leaves; 6) clear mosaic areas distributed over young leaves; 7) wide distribution of mosaic on young leaves and the plant shows mottling; 8) mosaic covers the complete surface of young leaves and severe mottling is present; 9) complete mosaic, yellowing and distortion of leaf shape for all young leaves of apex and shoots. If 90% of the susceptible control plants score within classes 7 to 9, then the trial can be deemed successful.

Example 2. Leaf Vein Necrosis Evaluation Assays

Vein necrosis is a morphological disorder that manifests on cucumber plants as necrosis spots around the veins of mature leaves. The severity of necrosis ranges from small necrotic spots around the main veins to whole leaf necrosis. The development of vein necrosis has been found to be genetic and its expression is influenced by genetic background. Under greenhouse conditions, vein necrosis is often observed in plants from the spring until fall. Because of the variability in vein necrosis manifestation and severity due to genetic background, pedigrees should be trialed in a randomized design, with a minimum of two replicates of four plants. The replicates should be designed to correct for light variation across plant rows. Plants should be grown using double planting rows between paths. Border effects should be reduced as much as possible by applying at least two border plants at the borders of the experiment. Plants can be grown either on perlite or Rockwool. The climate in the greenhouse should be set to a 20° C. day and 19° C. night cycle. No artificial light should be applied, and experiments should not be conducted in low light conditions typical during the November to February months in the Netherlands to avoid confusing vein necrosis caused by the genetics and necrosis caused by low light conditions. The plants should receive nutrients using a composition and frequency typical for cucumber greenhouse growing. Plants need to be grown using the umbrella system where only the main meristem is grown back down from the wire. No lateral shoots are grown up to the wire. Growth meristem can be removed when it reaches 1.2-1.5 meters above ground. No leaves should be removed. Female flowers need to be pruned to 1 female flower per node on the main stem. It is not necessary to prune lateral shoots. Fruits should be harvested regularly to maintain plant balance.

Vein necrosis becomes visible on mature leaves about 6-7 weeks after sowing, when the fruit load starts to increase. Formal evaluation of symptoms should be done at approximately 9-10 weeks after sowing, which is when negative controls such as Cornell Chinese Long, show high levels of vein necrosis. The level of necrosis is scored on a scale ranging from 1 to 9, where a 1 indicates an absence of vein necrosis and a 9 indicates high levels of vein necrosis between the veins on several leaves to complete leaf death. Intermediate levels are scored using the following criteria: 3: some small necrotic spots around the main nerves; 5: heavy vein necrosis limited to the nerves and some yellowing in the interveinal regions; 7: heavy vein necrosis around and in between the veins.

Example 3. Mapping the CGMMV Resistance QTLs in Cucumber

CGMMV resistance is controlled by a major quantitative trait locus (QTL) on chromosome 5. Commercial varieties containing the resistance locus on chromosome 5 do not exhibit the same level of resistance to CGMMV that is observed in the wild cucumber accession Cornell Chinese Long. Mapping populations using resistant commercial varieties and Cornell Chinese Long as donor parents were generated to determine the genetic basis of CGMMV resistance in Cornell Chinese Long. The CGMMV resistance locus on chromosome 5 was mapped to a 1.4 cM region between marker loci CGMMV_M1 and CGMMV_M2 (FIG. 1). Marker CGMMV_M1 is a SNP marker with a [T/G] change at 5,704,478 bp of chromosome 5 of the public cucumber genome v2 map. Marker CGMMV_M2 is a SNP marker with a [A/T] change at 6,345,266 bp of chromosome 5 of the public cucumber genome v2 map. Interstitial marker CGMMV_M3 was developed for selection of the CGMMV resistance locus on chromosome 5 and is a SNP marker with a [C/T] change at 5,889,044 bp of chromosome 5 of the public cucumber genome v2 map. Table 1 shows the markers that can be used to track the CGMMV resistance locus on chromosome 5. The resistance conferred by the locus is additive, and requires homozygous deployment to reach market acceptable resistance levels.

plants. The newly identified CGMMV resistance-enhancing QTL on chromosome 1 was therefore determined to be linked to severe leaf vein necrosis, a trait which can be seen in donor accession Cornell Chinese Long. This linkage drag associated with the introgression of the CGMMV resistance-enhancing locus on chromosome 1 renders otherwise desirable disease-resistant plants as unmarketable.

For fine-mapping of the CGMMV resistance-enhancing QTL on chromosome 1, the phenotypic scores of the sister lines used for rough mapping were analyzed for differences in haplotype in the QTL region on chromosome 1. More than 200 lines with recombination events in and around the mapped region on chromosome 1 were phenotyped for their resistance against CGMMV using the seedling assay. Lines with the same haplotype were pooled and these haplotype groups were tested for significant differences in CGMMV resistance. The results of this experiment reduced the QTL

TABLE 1

Markers to track CGMMV resistance locus on chromosome 5.

| Marker Name | Chr | Public position SNP (bp) | Marker size (bp) | SNP position in marker (bp) | SNP change | CCL allele | Marker Sequence Full, Core (SEQ ID NO) | Fwd Primer (SEQ ID NO) | Rev Primer (SEQ ID NO) | Probe 1 (SEQ ID NO) | Probe 2 (SEQ ID NO) |
|---|---|---|---|---|---|---|---|---|---|---|---|
| CGMMV_M1 | 5 | 5,704,478 | 121 | 61 | T/G | T | 1, 41 | 2 | 3 | 4 | 5 |
| CGMMV_M3 | 5 | 5,889,044 | 601 | 301 | C/T | T | 11, 43 | 12 | 13 | 14 | 15 |
| CGMMV_M2 | 5 | 6,345,266 | 269 | 136 | A/T | A | 6, 42 | 7 | 8 | 9 | 10 |

The mapping experiments confirmed that Cornell Chinese Long contains the major CGMMV resistance locus on chromosome 5 but also contains a minor locus on chromosome 1 that enhances the resistance conferred by the locus on chromosome 5. The locus on chromosome 1 was not found in the CGMMV resistant commercial varieties. The QTL on chromosome 1 was mapped using two F2:3 mapping populations made from a cross between Cornell Chinese Long and two different elite lines that are susceptible to CGMMV. Two populations were used to determine if the CGMMV resistance from Cornell Chinese Long is efficacious in different genetic backgrounds. The locus on chromosome 1 was mapped using backcross material from the initial mapping population that was fixed for the CGMMV resistance locus on chromosome 5. 31 sister line families where phenotyped for CGMMV symptom severity at the seedling stage, which mapped the CGMMV resistance-enhancing trait to a 8.4 cM region interval on chromosome 1. However, when the CGMMV resistance-enhancing QTL on chromosome 1 was introgressed into elite cucumber plants, a leaf vein necrosis phenotype also appeared in these region to a 1.8 cM interval on chromosome 1 between markers CGMMV_M4 and CGMMV_M5 (FIG. 1). In addition, marker CGMMV_M6 was developed within the QTL region on chromosome 1 to select the CGMMV resistance-enhancing QTL. Marker CGMMV_M4 is a SNP marker with a [C/T] change at 1,723,554 bp of chromosome 1 of the public cucumber genome v2 map. Marker CGMMV_M5 is a SNP marker with a [C/T] change at 2,141,985 bp of chromosome 1 of the public cucumber genome v2 map. Interstitial marker CGMMV_M6 is a SNP marker with a [A/G] change at 1,926,358 bp of chromosome 1 of the public cucumber genome v2 map. Table 2 shows the markers that can be used to track the CGMMV resistance-enhancing locus on chromosome 1.

TABLE 2

Markers to track CGMMV resistance-enhancing locus and leaf vein necrosis trait on chromosome 1.

| Marker Name | Chr | Public position SNP (bp) | Marker size (bp) | SNP position in marker (bp) | SNP change | CCL allele | Marker Sequence Full, Core (SEQ ID NO) | Fwd Primer (SEQ ID NO) | Rev Primer (SEQ ID NO) | Probe 1 (SEQ ID NO) | Probe 2 (SEQ ID NO) |
|---|---|---|---|---|---|---|---|---|---|---|---|
| CGMMV_M4 | 1 | 1,723,554 | 1029 | 855 | C/T | T | 16, 44 | 17 | 18 | 19 | 20 |
| CGMMV_M6 | 1 | 1,926,358 | 400 | 212 | A/G | G | 26, 46 | 27 | 28 | 29 | 30 |
| CGMMV_M5 | 1 | 2,141,985 | 493 | 344 | C/T | C | 21, 45 | 22 | 23 | 24 | 25 |
| CGMMV_M7 | 1 | 2,879,227 | 121 | 61 | A/G | A | 31 | 32 | 33 | 34 | 35 |
| CGMMV_M8 | 1 | 3,791,533 | 121 | 61 | T/G | T | 36 | 37 | 38 | 39 | 40 |

Example 4. Mapping of the Vein Necrosis Trait on Chromosome 1

Figure 2:
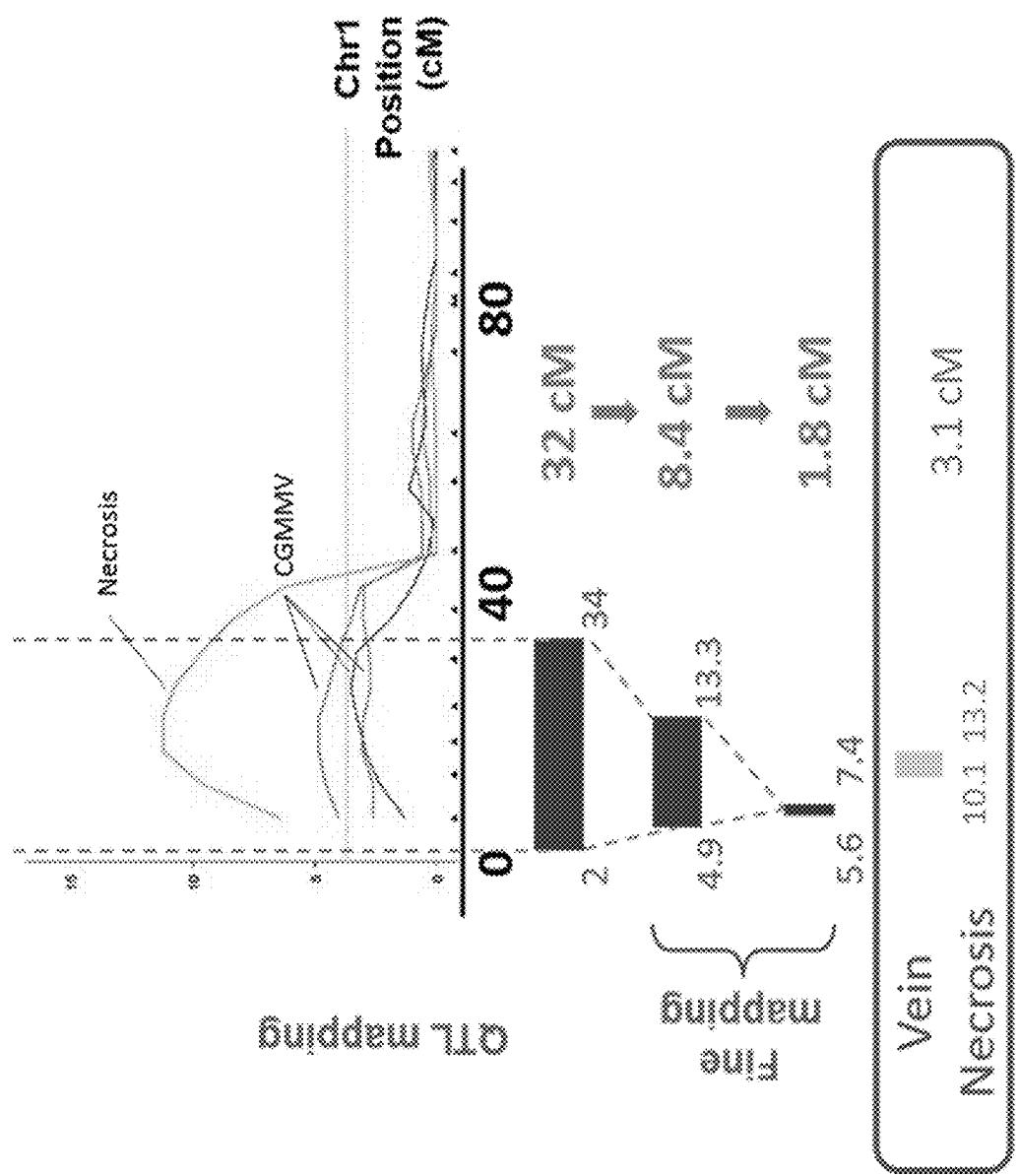
FIG. 2: Shows a diagram of the mapping process for the CGMMV resistance-enhancing introgression from Cornell Chinese Long on chromosome 1. This also shows the uncoupling of leaf vein necrosis locus on chromosome 1.

The rough mapping of the vein necrosis trait was done simultaneously in the two populations that were used for the mapping of the resistance locus on chromosome 1. The QTL analysis revealed a locus on chromosome 1 that explained the genetic variation for vein necrosis. This QTL co-localizes with the CGMMV resistance-enhancing QTL identified on the same chromosome. It was observed that the maximum level of vein necrosis differed between the two mapping populations. One population was observed as having a maximum symptom score of 2, which was not significantly higher than the non-necrotic lines. The other population had a maximum score of 7, which was more desirable for fine-mapping of the trait due to the more visible phenotype. This population was used for further fine-mapping of the vein necrosis trait locus accordingly. 54 lines containing a recombination event within the rough mapped region of the CGMMV resistance-enhancing QTL on chromosome 1 were used for analysis. These lines were phenotyped for vein necrosis and lines with the same haplotype were pooled. The subsequent analysis mapped the trait to a 3.1 cM region between markers CGMMV_M7 and CGMMV_M8. Marker CGMMV_M7 is a SNP marker with a [A/G] change at 2,879,227 bp of chromosome 1 of the public cucumber genome v2 map. Marker CGMMV_M8 is a SNP marker with a [T/G] change at 3,791,533 bp of chromosome 1 of the public cucumber genome v2 map (Table 2). This region is closely linked to the 1.8 cM CGMMV resistance-enhancing QTL on chromosome 1 at a distance of 2.65 cM (FIG. 2). Identification of this region enabled the production of elite plants having the CGMMV resistance QTLs on chromosomes 1 and 5 and lacking the leaf vein necrosis trait from chromosome 1. Thus, markers CGMMV_M7 and CGMMV_M8 may be used to select against the leaf vein necrosis trait on chromosome 1.

Example 5. Efficacy of Stacking the QTLs on Chromosome 5 and Chromosome 1

Using marker-assisted backcrossing, two lines were developed in the same elite genetic background. This genetic background was fully susceptible to CGMMV, ensuring that only the effects of the resistance QTL on chromosome 5 from Cornell Chinese Long or the combination of the QTLs on chromosomes 1 and 5 from Cornell Chinese Long were measured. These conversions were screened for CGMMV symptoms severity at the mature plant stage. In addition, these converted lines were evaluated along with commercial hybrids to determine how the resistance QTLs from Cornell Chinese Long compared to already available commercial resistant varieties. The base level of CGMMV symptoms were scored at a 7 out of 9 (1=fully resistant, 9=fully susceptible) for the susceptible recurrent parent. Plants that were homozygous for the resistance QTL on chromosome 5 scored a 4 out of 9, which is considered to be intermediate resistance. Plants that were homozygous for the resistance QTL on chromosome 5 and also contained the QTL on chromosome 1 scored a 3 out of 9, which is considered to be high resistance. These results show that the QTL on chromosome 1 enhances the CGMMV resistance conferred by the locus on chromosome 5.

What is claimed is:

1. An agronomically elite *Cucumis sativus* plant comprising a recombinant chromosomal segment on chromosome 1 and a recombinant chromosomal segment on chromosome 5, wherein said recombinant chromosomal segment on chromosome 5 confers increased resistance to Cucumber Green Mottle Mosaic Virus (CGMMV) relative to a *Cucumis sativus* plant that lacks said recombinant chromosomal segment, and wherein said recombinant chromosomal segment on chromosome 1 confers increased resistance to CGMMV in a *Cucumis sativus* plant that comprises said recombinant chromosomal segment on chromosome 5 relative to a *Cucumis sativus* plant that comprises the recombinant chromosomal segment on chromosome 5 and lacks said recombinant chromosomal segment on chromosome 1, wherein said recombinant chromosomal segment on chromosome 1 comprises marker locus CGMMV_M6 (SEQ ID NO: 26), and wherein said recombinant chromosomal segment on chromosome 5 comprises marker locus CGMMV_M3 (SEQ ID NO: 11).

2. The plant of claim 1, wherein said recombinant chromosomal segment on chromosome 1 or said recombinant chromosomal segment on chromosome 5 comprises an allele conferring said increased resistance to CGMMV that is obtainable from *Cucumis sativus* accession Cornell Chinese Long, a representative sample of seed of said accession having been deposited under ATCC Accession No. PTA-126674.

3. The plant of claim 1, wherein said recombinant chromosomal segment on chromosome 1 that confers resistance to CGMMV is located between 1,723,554 bp and 2,141,985 bp on chromosome 1 of the public cucumber genome v2 map and wherein said recombinant chromosomal segment on chromosome 5 that confers resistance to CGMMV is located between 5,704,478 bp and 6,345,266 bp on chromosome 5 of the public cucumber genome v2 map.

4. The plant of claim 1, wherein said recombinant chromosomal segment on chromosome 1 lacks a deleterious allele genetically linked thereto that confers to the plant a leaf vein necrosis phenotype when present, and wherein said recombinant chromosomal segment on chromosome 1 lacks a donor plant allele at marker locus CGMMV_M7 (SEQ ID NO: 31) or marker locus CGMMV_M8 (SEQ ID NO: 36).

5. The plant of claim 1, defined as an inbred or hybrid plant.

6. A seed that produces the plant of claim 1.

7. A plant part of the plant of claim 1, wherein said plant part comprises the recombinant chromosomal segment on chromosome 1 and the recombinant chromosomal segment on chromosome 5.

8. The plant part of claim 7, wherein the part is selected from a stem, petiole, cotyledon, flower, anther, pollen, ovary, root, root tip, protoplast, ovule, shoot, embryo, embryo sac, bud, leaf, meristem or cell.

9. The plant of claim 1, wherein said recombinant chromosomal segment on chromosome 1 further comprises a marker locus selected from marker locus CGMMVM4 (SEQ ID NO: 16) or marker locus CGMMV_M5 (SEQ ID NO: 21) and wherein said recombinant chromosomal segment on chromosome 5 further comprises a marker locus selected from CGMMV_M1(SEQ ID NO: 1) or marker locus CGMMVM2 (SEQ ID NO: 6) on chromosome 5.

* * * * *